(12) United States Patent
Workman

(10) Patent No.: US 7,415,890 B2
(45) Date of Patent: Aug. 26, 2008

(54) UNBONDED SYSTEM FOR STRENGTH TESTING OF CONCRETE MASONRY UNITS

(75) Inventor: Gary Workman, Lombard, IL (US)

(73) Assignee: Deslauriers, Inc., LaGrange Park, IL (US)

( * ) Notice: Subject to any disclaimer, the term of this patent is extended or adjusted under 35 U.S.C. 154(b) by 605 days.

(21) Appl. No.: 10/712,943

(22) Filed: Nov. 13, 2003

(65) Prior Publication Data

US 2005/0106379 A1    May 19, 2005

(51) Int. Cl.
  *G01N 3/08*   (2006.01)
  *B32B 3/26*   (2006.01)

(52) U.S. Cl. .............................. 73/818; 73/803; 73/860; 428/304.4

(58) Field of Classification Search .............. 428/304.4; 73/788, 845, 803, 860, 866; 52/309.12
See application file for complete search history.

(56) References Cited

U.S. PATENT DOCUMENTS

| | | | |
|---|---|---|---|
| 2,414,559 A | 1/1947 | Patch et al. | |
| 3,295,278 A * | 1/1967 | Muhm | 52/223.6 |
| 3,545,263 A | 12/1970 | Hadley et al. | |
| 4,445,387 A | 5/1984 | Hall et al. | |
| 4,534,225 A * | 8/1985 | Peacock et al. | 73/860 |
| 4,566,558 A * | 1/1986 | Link et al. | 181/210 |
| 4,740,025 A | 4/1988 | Nelson | |
| 5,695,870 A * | 12/1997 | Kelch et al. | 428/318.4 |
| 6,276,104 B1 * | 8/2001 | Long et al. | 52/309.4 |
| 6,591,691 B2 | 7/2003 | Kim et al. | |

OTHER PUBLICATIONS

"Econ-O-Cap" Product Guide, Deslauriers, Inc.

* cited by examiner

*Primary Examiner*—Hai Vo
*Assistant Examiner*—Anish Desai
(74) *Attorney, Agent, or Firm*—Wood, Phillips, Katz, Clark & Mortimer

(57) ABSTRACT

An unbonded capping system for strength testing of concrete masonry units (CMUs) comprises a rigid, rectangular foam board of a size to be received on a face of a CMU. A plastic sheet is laminated to the rigid foam board and is engagable by a test apparatus, in use, with the rigid foam board engaging the face of the CMU to provide even load distribution during testing.

6 Claims, 1 Drawing Sheet

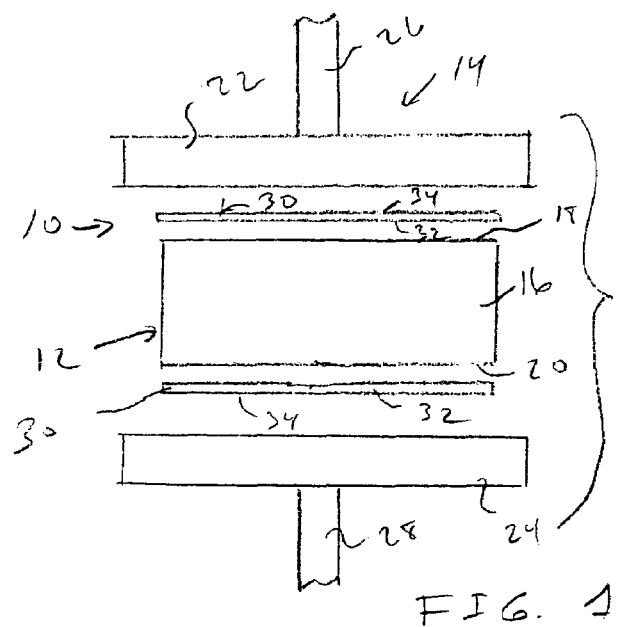
FIG. 1
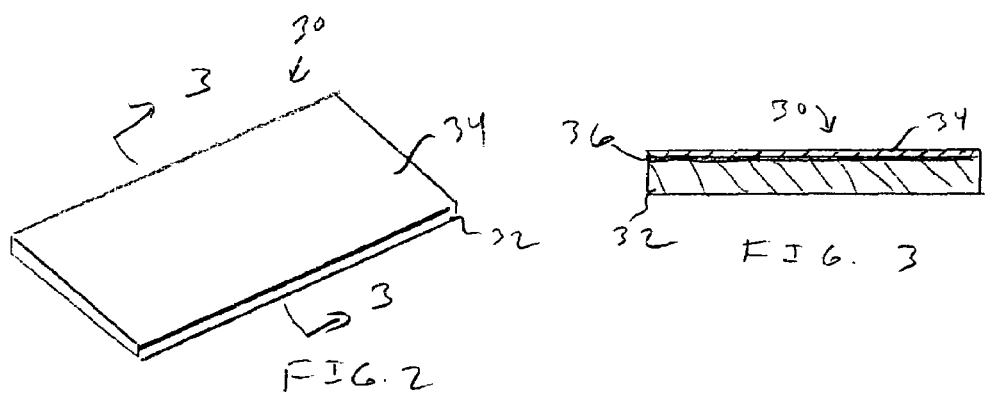
FIG. 2
FIG. 3

UNBONDED SYSTEM FOR STRENGTH TESTING OF CONCRETE MASONRY UNITS

FIELD OF THE INVENTION

This invention relates to strength testing of concrete masonry units, and more particularly, to an unbonded capping system.

BACKGROUND OF THE INVENTION

Masonry walls are typically constructed using concrete masonry units (CMUs). CMUs are sometimes referred to as cinder blocks. A CMU consists of a hollow, rectangular building block having one or more vertical cavities. CMUs may be tested according to ASTM standard C140 for dimensions, compressive strength, absorption, unit weight (density), and moisture content. Traditionally, the test for compressive strength is performed by capping CMUs with either a sulfur capping compound or a gypsum capping compound. The capping process is labor intensive and costly since the mortar must be mixed, the CMUs capped, and the mortar must harden. The sulfur compound hardens more quickly, but can be hazardous since the sulfur mixes with the humidity in the air to form sulfuric acid. The gypsum compound can be safer, but takes longer to set up.

Alternatives have been used for quicker strength tests of CMUs using, for example, gypsum board, wood veneer or commercial ceiling tiles. The gypsum board and wood veneer yield low indicated strengths. The ceiling tiles do not have consistency of density, weight etc., and can absorb moisture. Also, any of these products must be cut to fit and can be easily damaged during cutting, fitting and handling.

The present invention is directed to solving one or more of the problems discussed above in a novel and simple manner.

SUMMARY OF THE INVENTION

In accordance with the invention, there is provided an unbonded capping system for strength testing of concrete masonry units.

In accordance with one embodiment of the invention there is disclosed an unbonded capping system for strength testing of concrete masonry units (CMUs). The system comprises a rigid, rectangular foam board of a size to be received on a face of a CMU. A plastic sheet is laminated to the rigid foam board and is engagable by a test apparatus, in use, with the rigid foam board engaging the face of the CMU to provide even load distribution during testing.

It is a feature of the invention that the rigid foam board comprises an expanded polystyrene (EPS) foam board. The EPS foam board may have a density greater than 2 lb/ft$^3$ and advantageously may have a density of about 3 lb/ft$^3$.

It is another feature of the invention that the foam board has a thickness of about 0.5 inches and the plastic sheet has a thickness of about 0.06 inches.

It is a further feature of the invention that the plastic sheet is laminated to the rigid foam board with an adhesive.

There is disclosed in accordance with another embodiment of the invention a pair of compression pads for use with a testing system for compression testing of CMUs including first and second platens. Each compression pad comprises a rigid, rectangular foam board of a size to be received on one face of a CMU. A plastic sheet is laminated to the rigid foam board and is engagable by one of the test platens, in use, with the rigid foam board engaging the face of the CMU to provide even load distribution during testing.

There is disclosed in accordance with still another embodiment of the invention an improvement in a capping system for compression testing of CMUs including first and second platens. The improvement comprises a pair of laminated compression pads. Each comprises a rigid, rectangular foam layer of a size to be received on one face of a CMU, and a plastic sheet layer laminated to the rigid foam layer and engagable by one of the test platens, in use, with the rigid foam layer engaging the face of the CMU to provide even load distribution during testing.

There is disclosed in accordance with a still further embodiment of the invention an unbonded capping system for strength testing of concrete masonry units comprising a pair of laminated compression pads. Each laminated compression pad comprises a high density expanded polystyrene foam layer of a size to be received on a face of a concrete masonry unit, and a plastic sheet layer adhered to the EPS foam layer and engagable by test apparatus, in use, with the EPS foam layer engaging the face of the CMU to provide even load distribution during testing.

Further features and advantages of the invention will be readily apparent from the specification and from the drawings.

BRIEF DESCRIPTION OF THE DRAWINGS

FIG. 1 is an exploded, side view of an unbonded capping system in accordance with the invention for strength testing of a concrete masonry unit;

FIG. 2 is a prospective view of a compression pad of the unbonded capping system of FIG. 1; and FIG. 3 is a sectional view taken along the line 3-3 of FIG. 2.

DETAILED DESCRIPTION OF THE INVENTION

In accordance with the invention, there is provided an unbonded capping system 10, see FIG. 1, for compression testing of a concrete masonry unit (CMU) 12. The unbonded capping system 10 is adapted to use with a compression testing apparatus or fixture 14.

The CMU 12 can be formed using any known technique. The conventional CMU 12 is about sixteen inches long and most typically comes in widths of eight, ten and twelve inches. The CMU 12 comprises a concrete block 16 having vertical cavities (not shown) therethrough between an upper face 18 and a lower face 20.

The testing apparatus 14 includes a first platen 22 and a second platen 24. The platens 22 and 24 are operated by any known means, illustrated schematically as pistons 26 and 28. In a typical test for compressive strength, the platens 22 and 24 compress the CMU 12 to failure in a conventional manner. In accordance with the invention, the unbonded capping system 10 provides a quick strength test of the CMU 12 without being bonded to the CMU 12.

The unbonded capping system comprises a pair of laminated compression pads 30. Each compression pad 30 is identical in construction and is illustrated greater detail in FIGS. 2 and 3.

The compression pad 30 comprises a rigid, rectangular foam board or layer 32 of a size to be received on one face 18 or 20 of the CMU 12. A rigid plastic sheet 34 is laminated to the foam board 32 with an adhesive layer 36. The plastic sheet 34 is engagable by one of the test platens 22 or 24, in use, with the rigid foam board 32 engaging the corresponding respective face 18 or 20 of the CMU 12 to provide even load distribution during testing.

In accordance with the invention, the foam board 32 comprises a high density foam board which may be of, for example, expanded polystyrene (EPS). EPS comprises a polymer impregnated with a foaming agent which is exposed to steam to create a uniform closed cell structure highly resistant to heat flow and moisture penetration. The EPS is fused into a block and cured and then cut into a board of an appropriate size. While the EPS could be formed of various different densities, advantageously, the EPS is a high density EPS greater than 2 lbs/ft$^3$ and, advantageously, about 3 lbs/ft$^3$. In the illustrated embodiment of the invention, the foam board 32 has a thickness of 0.50 inches.

The plastic sheet 34 may be formed of various different plastics and is utilized to provide protection to the platens 22 and 24 during testing and to protect the foam board 32 from damage during handling. In an illustrated embodiment of the invention, the plastic sheet 34 has a thickness of approximately 0.060 inches.

Standard CMUs are typically eight, ten or twelve inches wide and sixteen inches long, as noted above. The compression pad 30 is similarly about sixteen inches long and selectively has a width of eight, ten or twelve inches according to the size of the CMU 12 to be tested. Thickness is about 0.56 inches.

In use, and referring again to FIG. 1, two compression pads 30 are used one on top and one on the bottom of the CMU 12 to be tested. Particularly, the compression pad 30 is oriented so that the plastic sheet 34 is engageable by a test platen 22 or 24 and the foam board 32 engages the face 18 or 20 of the CMU 12. The CMU 12 is tested to failure in the conventional manner. The plastic sheet 34 provides rigidity for the foam board 32 and protects the platens 22 and 24 of the testing machine. The foam of the board 32 flows into irregularities of the CMU 12 insuring the load is distributed evenly.

The use of the high density EPS foam board 32 provides consistency in density and test results as the foam does not absorb moisture which can change test results from one batch to another. Also, the foam does not grab stems between cells in the block 16 which could cause them to break, resulting in bad test results.

Thus, in accordance with the invention, there is described an unbonded capping system for compression testing of concrete cylinders.

I claim:

1. In a testing system for compression testing of concrete masonry units including first and second platens, the improvement comprising a pair of compression pads each comprising:
   a rigid, rectangular foam board of a size to be received on one face of a concrete masonry unit; and
   a plastic sheet laminated to the rigid foam board and being engageable by one of the test platens, in use, with the rigid foam board engaging the face of the concrete masonry unit to provide even load distribution during testing.

2. The compression pads of claim 1 wherein the rigid foam board comprises an expanded polystyrene (EPS) foam board.

3. The compression pads of claim 2 wherein the EPS foam board has a density greater than 2 lb/ft3.

4. The compression pads of claim 2 wherein the EPS foam board has a density of about 3 lb/ft3.

5. The compression pads of claim 1 wherein the foam board has a thickness of about 0.5 inches and the plastic sheet has a thickness of about 0.06 inches.

6. The compression pads of claim 1 wherein the plastic sheet is laminated to the rigid foam board with an adhesive.

\* \* \* \* \*